United States Patent [19]

Hori et al.

[11] Patent Number: 4,762,427
[45] Date of Patent: Aug. 9, 1988

[54] SENSOR FOR MEASUREMENT BY ELECTRICAL HEATING

[75] Inventors: Tomoshige Hori, Kitamoto; Kensuke Itoh, Kodaira, both of Japan

[73] Assignee: Snow Brand Milk Products Co., Ltd., Sapporo, Japan

[21] Appl. No.: 71,565

[22] Filed: Jul. 9, 1987

Related U.S. Application Data

[63] Continuation of Ser. No. 830,944, Feb. 19, 1986, abandoned.

[30] Foreign Application Priority Data

Sep. 6, 1985 [JP]  Japan ................................ 197230

[51] Int. Cl.$^4$ ............................ G01K 1/08; G01K 1/14
[52] U.S. Cl. ........................................ 374/141; 374/16; 374/185; 426/231
[58] Field of Search ................ 374/45, 25, 26, 103, 374/141, 185; 338/25, 26, 302

[56] References Cited

U.S. PATENT DOCUMENTS

| | | | |
|---|---|---|---|
| 2,730,597 | 1/1956 | Podolsky et al. | 338/302 X |
| 3,034,542 | 5/1962 | Blanco | 338/302 X |
| 3,845,443 | 10/1974 | Fisher | 338/25 |
| 3,939,557 | 2/1976 | Randle | 338/25 X |
| 4,462,020 | 7/1984 | May | 338/302 X |
| 4,663,169 | 5/1987 | Hori et al. | 374/16 X |

Primary Examiner—Daniel M. Yasich
Attorney, Agent, or Firm—Murray and Whisenhunt

[57] ABSTRACT

A sensor for measuring the temperature of a liquid or semi-solid material by electrical heating. A core rod has disposed thereon a first electrically insulating member and a thin metal wire is wound about the first insulating member on the core rod. A second electrically insulating member covers the thin metal wire. When an electrical current is passed through the thin metal wire heat is generated in the thin metal wire. The resistance in the thin metal wire is proportional to the temperature thereof, which temperature is proportional to the current passed through the thin metal wire and the temperature of the liquid or semi-solid in which the sensor with the thin metal wire is disposed. Thus the temperature of the liquid or semi-solid can be determined by measuring the voltage or resistance in the thin metal wire by known measuring devices.

5 Claims, 4 Drawing Sheets

SENSOR FOR MEASUREMENT BY ELECTRICAL HEATING

This application is a continuation of Ser. No. 830,944, filed Feb. 19, 1986, now abandoned.

BACKGROUND OF THE INVENTION

This invention relates to a sensor used for a so-called electrical heating measurement in which a metal member is inserted in various liquid materials or semi-solid materials, the metal member is heated under the application of electrical current to result in higher temperature than those of said materials, and changes in parameter of the metal member are continuously measured in relation to time lapse to detect changes in state of the materials.

The inventors of this application have already proposed, in Japanese Patent Application No. 58-92079, a measuring method as below. According to this method, in a milk curdling process, a thin metal wire is inserted in milk stored in a tank, an electrical current is passed intermittently or continuously through the thin metal wire for measurement of temperatures of the thin metal wire in relation to time lapse, and a curdy state of milk is judged from a measurement result. In this method, a sensor made of a straight platinum wire of 0.1 mm diameter and 106 mm length is used. The sensor of platinum wire is however disadvantageous in that the platinum wire will be broken when intensively pressed by fingers, that a tank whose interior surface is not applied with insulating treatment will possibly be eroded to perforate under the influence of electrolytic corrosion when the sensor is used for a long time, and that even though the entire length of the sensor is relatively large, a large amount of electrical current is required for heating.

SUMMARY OF THE INVENTION

This invention contemplates elimination of the above drawbacks of the conventional sensor, and has for its objective to provide a shock-proof sensor which does not erode the tank under the influence of electrolytic corrosion and which can reduce the amount of current required for heating.

According to this invention, the above objective can be accomplished by a sensor comprising a core rod covered with an electrically insulating member, a thin metal wire wound about the core, and an electrically insulating member covering the thin metal wire. Specifically, assuming that the amount of heat generated in the wire is W, the amount of current supplied to the wire is I and the resistance of the wire is R, W is given by $W = I^2 R$, indicating that the generated heat increases in proportion to the resistance. Since, in the sensor according to the invention, the thin metal wire is wound about the core rod so that the length of the wire can be increased as compared to the straight wire, the amount of generated heat per unit length of the sensor is increased proportionally, thereby making it possible to reduce the amount of current, as compared to that of the conventional sensor, for obtaining the same sensitivity. Further, for the sake of obtaining the same amount of heat generation, the length of the sensor according to the invention can be decreased as compared to that of the conventional sensor.

In addition, the thin metal wire wound about the core rod is improved in its shock proof properties and is therefore difficult to break. Also, the thin metal wire covered, interiorly and exteriorly thereof, with the electrically insulating members will not erode the tank under the influence of electrolytic corrosion.

DESCRIPTION OF THE PREFERRED EMBODIMENT

Figure 1:
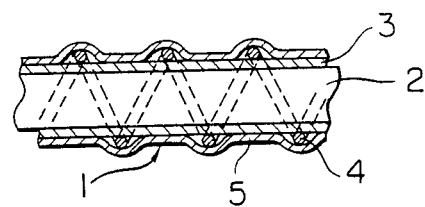
FIG. 1 is a fragmental longitudinally sectional front view of a sensor according to an embodiment of the invention.

FIG. 1 shows a fragmentary sectional view of sensor 1 embodying the invention. The sensor 1 has a core rod 2 such as a stainless steel rod, an electrically insulating member 3 made of, for example, Teflon, a metal wire 4 made of, for example, platinum and helically wound about the electrically insulating member 3, and an electrically insulating member 5 made of the same material as the member 3 and covering the metal wire 4.

FIGS. 2A to 2G show the manufacture steps of the sensor.

Figures 2A, 2B:
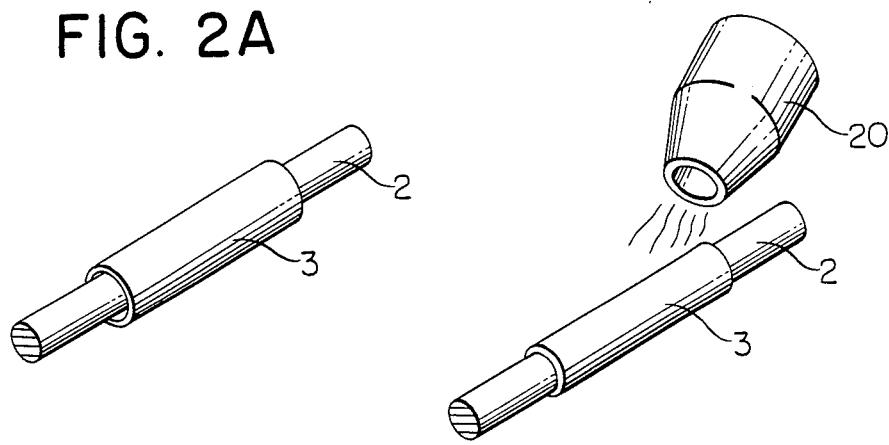
FIGS. 2A to 2G are diagrams sequentially illustrating manufacture steps of the embodiment.
Figure 2C:
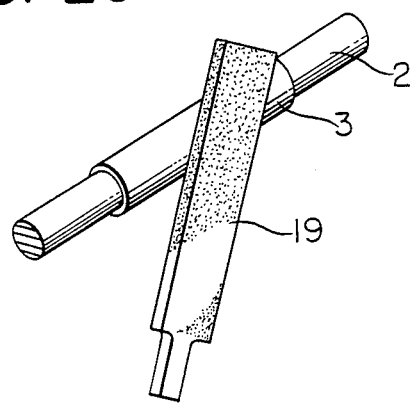
Figure 2D:
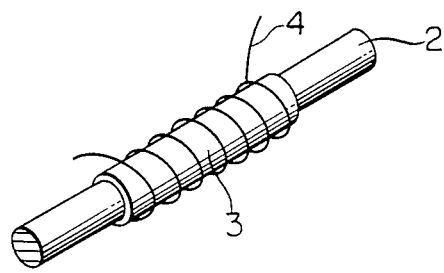
Figure 2E:
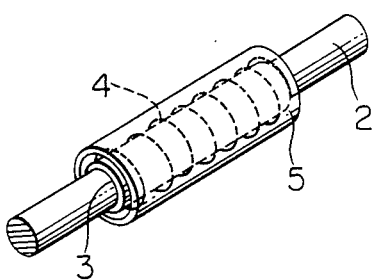
Figure 2F:
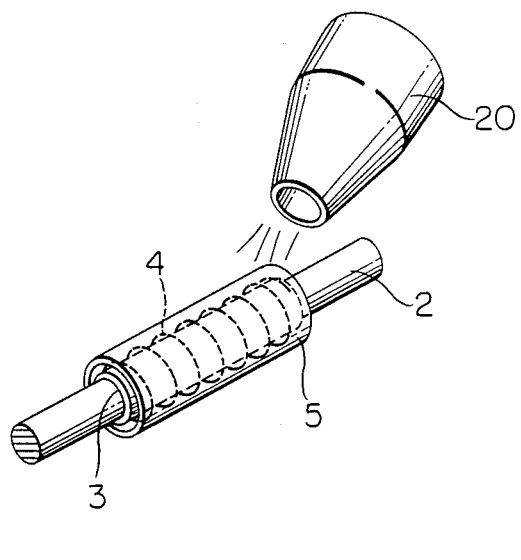
Figure 2G:
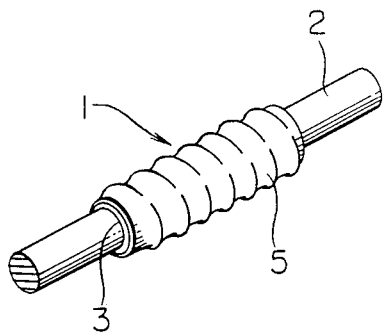

In FIG. 2A, a stainless steel rod 2 of 2 mm diameter is first covered with a thermally contractible tube 3 of Teflon having an inner diameter of 3 mm, and as shown in FIG. 2B the tube 3 is heated and contracted by blowing hot air at about 400° C. from a burner 20. Subsequently, as shown in FIG. 2C, the surface of the Teflon cover is finished with a file 19, and a platinum wire 4 is helically wound about the finished surface and slightly bonded thereto with an adhesive, as shown in FIG. 2D. thereafter, a thermally contractible tube 5 made of Teflon and having an inner diameter of 3 mm is applied on the platinum wire coil as shown in FIG. 2E and heated for contraction by blowing hot air at about 400° C. from the burner 20, as shown in FIG. 2F. Thus, a sensor 1 is completed as shown in FIG. 2G.

Figure 3:
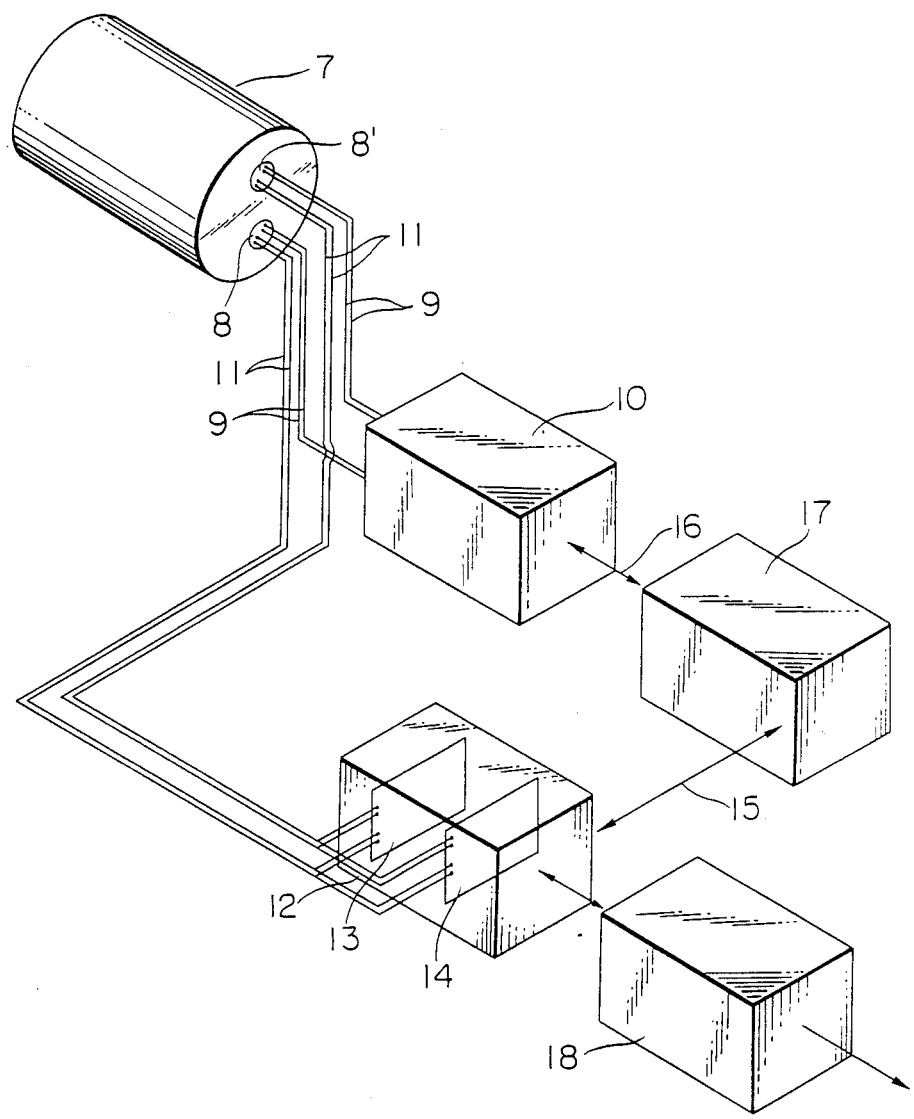
FIG. 3 is a schematic diagram of an automatic measurement and control system for a curd making process in which the sensor is exemplarily used.
Figure 4:
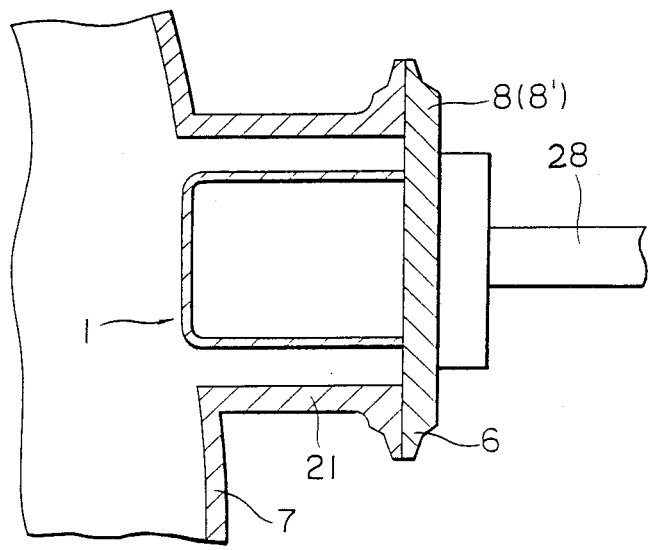
FIG. 4 is a fragmentary sectional front view showing the state of the sensor used in the system of FIG. 3.

For example, to carry out automatic measurement and control in curd making process with a system as shown in FIG. 3, two of the thus prepared sensors 1 are respectively fixed to flange plates 6 as shown in FIG. 4 to constitute sensor units 8 and 8', and sensor units are respectively mounted to whey discharge flanges 21 which extend from an end wall of a lateral type cylindrical cheese tank of about 20 m$^3$ capacity and 4 m diameter at heights thereof corresponding to 5 m$^3$ and 12 m$^3$ levels.

The sensor units 8 and 8' are supplied with an electrical current for measurement of voltage through multi-core cables 28 shielded with a copper tape and composed of signal wires each having a crosssectional area of 1.25 mm$^2$, so that electrical resistance of each sensor can be measured on the basis of a four-wire method. As shown in FIG. 3, four current lead wires 9 connected to the signal wires connect to a DC power supply 10 which is controlled by a controller 17 comprised of a computer, and the other four voltage lead wires 11 connect to an A/D converter 13 and a relay card 14 of a data loader (data collecting controller) 12.

The data loader 12 and the power supply 10 are connected to the controller 17 through GP-IB cables 15 and 16, respectively. All instructions necessary for measurement and sequence control are issued in accordance with a program pursuant to a standard curd characteristic curve which has been read in the controller.

These instructions are fed via a sequence control system 18 to drive a motor, for example. The standard curd characteristic curve is representative of changes in temperature or electrical resistance of the thin metal wire of the sensor in relation to time lapse and illustrated in FIG. 5.

Figure 5:
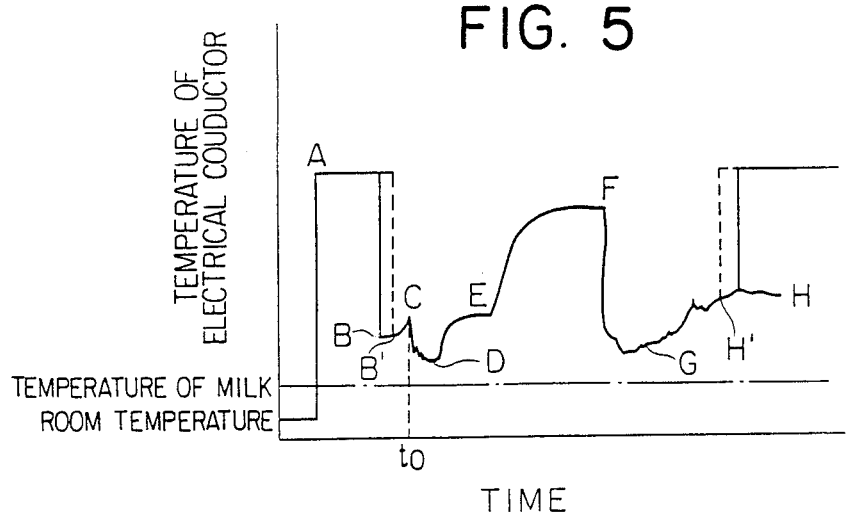
FIG. 5 is a graph showing a curd characteristic.

In FIG. 5, B and B' denote temperatures of the thin metal wires when supplying milk, C a metal wire temperature when adding rennet, D a metal wire temperature at the termination of stirring, E a metal wire temperature at the commencement of curdling, F a metal wire temperature at the commencement of curd cutting, G changes in metal wire temperature when cooking, and H and H' temperatures of metal wires when discharging whey.

For automatic control of cheese curd production by controlling the above parameters, the controller 17 first instructs the automatic power supply 10 to start supplying a constant DC current to the sensors 1 and the data loader 12 to start measuring voltages.

Measured voltages are sent to the controller 17 so as to be converted into corresponding temperatures or electrical resistances which in turn are used to display a temperature versus time curve or an electrical resistance versus time curve on a cathode ray tube attached to the controller 17. When the commencement of curdling represented by E is detected after completion of supply of milk, a timer included in the controller is actuated for a predetermined time, followed by transmittal of a signal for curd cutting to the sequence control system 18 and consequent actuation of a motor (not shown) for rotating cutting blades.

Finally, whey discharge is detected and measurement results are delivered out to a printer and a magnetic disc, ending an operation.

Specifically, the sensor 1 has a stainless steel rod 2 of 2 mm diameter and 5 cm length, a Teflon member 3 of 0.15 mm thickness covering the rod 2, a platinum wire 4 of 0.1 mm diameter wound about the Teflon member 3 by ten terns per 1 cm of the stainless steel rod 2, and a Teflon member 5 of 0.15 mm thickness covering the coiled platinum wire 4.

If the thickness of the outer Teflon member of the sensor 1 is large, then response time will be increased. Therefore, practically, the outer Teflon member preferably has a thickness which approximates the diameter of the platinum wire 4. The lower limit of this thickness may desirably be defined within a range over which mechanical strength and electrical insulation of the outer Teflon member can be warranted and leakage of current can be prevented. When the sensor 1 is applied to foodstuffs such as cheese, this sensor must be cleanned for sterilization by using chemicals of strong alkali and strong acid. Therefore, the outer cover is preferably heat-proof and chemicals-proof and its plasticizer is desired to be insoluble from the standpoint of sanitation of foodstuffs.

The thickness of the inner Teflon member 3 of the sensor 1 may desirably be selected but is preferably defined within a range over which mechanical strength and electrical insulation of the inner Teflon member can be warranted and heat dissipation can be prevented sufficiently.

In addition, the pitch of the metal wire coil must be increased in proportion to an expected amount of heat generation. Further, if the metal wire is wound by a number of turns which is more than ten per 1 mm length of the stainless steel rod, the output will disadvantageously become unstable.

Although a particular preferred embodiment of the invention has been disclosed in detail for illustrative purposes, it will be recognized that variations or modifications of the disclosed apparatus, including the rearrangement of parts, lie within the scope of the present invention.

What is claimed is:

1. A sensing and measuring device for measurement of temperature in a liquid or semi-solid food material by electrical heating comprising:
   a sensor comprising
      a stainless steel rod;
      a first thermally contractible electrially insulating member covering said stainless steel rod;
      a thin platinum wire wound about said first electrically insulating member;
      a second thermally contractible electrically insulating member covering said thin platinum wire, said second electrically insulating member being heat-proof and resistant to strong alkali and strong acid;
   means connected to said thin platinum wire for passing a constant DC current through said thin platinum wire, whereby heat is generated in said thin platinum wire such that said wire and said metallic core are heated to a temperature higher than the temperature of said food material; and
   measurement means connected to said thin platinum wire for measuring the voltage in said platinum wire while the said constant DC current is flowing threrethrough, so that the temperature of said food material can be determined from the voltage in said thin platinum wire, which voltage is proportioned to the temperature of said food material.

2. The device of claim 1, wherein both the first and second electrically insulating members are made of heat contractible Teflon.

3. The device of claim 1, wherein the thickness of the second electrically insulating member approximates the diameter of the thin metal wire.

4. The device of claim 1, wherein the thin metal wire is wound about the said first electrically insulating member by a number of turns which is no more than 10 turns per mm. length of the said core rod.

5. The device of claim 1, wherein said second electrically insulating member contains a plasticizer and said plasticizer is insoluble in said food material.

* * * * *